United States Patent
Kim et al.

(10) Patent No.: US 8,003,850 B2
(45) Date of Patent: Aug. 23, 2011

(54) METHOD FOR PRODUCING TARGET PROTEINS USING AMINO ACIDS AND PYRUVIC ACIDS IN CULTURE OF PLANT CELLS

(75) Inventors: Sang-Lin Kim, Seoul (KR);
Hyun-Kwang Tan, Seoul (KR);
Sang-Min Lim, Incheon-si (KR);
Wuk-Sang Ryu, Gunpo-si (KR);
Hahn-Sun Jung, Gunpo-si (KR);
Song-Jae Lee, Seoul (KR); Cheon-Ik Park, Anyang-si (KR); Seung-Hoon Kang, Ansan-si (KR); Dong-Il Kim, Incheon-si (KR)

(73) Assignee: Boryung Pharmaceutical Co., Ltd., Seoul (KR)

( * ) Notice: Subject to any disclaimer, the term of this patent is extended or adjusted under 35 U.S.C. 154(b) by 211 days.

(21) Appl. No.: 12/160,049

(22) PCT Filed: Sep. 19, 2007

(86) PCT No.: PCT/KR2007/004543
§ 371 (c)(1),
(2), (4) Date: Oct. 1, 2008

(87) PCT Pub. No.: WO2008/038932
PCT Pub. Date: Apr. 3, 2008

(65) Prior Publication Data
US 2009/0181428 A1    Jul. 16, 2009

(30) Foreign Application Priority Data

Sep. 25, 2006 (KR) .................. 10-2006-0093112
Sep. 19, 2007 (KR) .................. 10-2007-0095146

(51) Int. Cl.
*C12N 15/63* (2006.01)
*C12N 15/00* (2006.01)
*C12N 15/82* (2006.01)
*A01H 5/00* (2006.01)

(52) U.S. Cl. ........ 800/284; 800/278; 800/290; 800/295; 435/320.1; 435/468

(58) Field of Classification Search .................. None
See application file for complete search history.

(56) References Cited

U.S. PATENT DOCUMENTS

| 5,460,952 | A | 10/1995 | Yu et al. |
| 5,693,506 | A | 12/1997 | Rodriguez |
| 6,642,434 | B1 | 11/2003 | Dellapenna et al. |
| 2002/0120953 | A1 | 8/2002 | McDonald et al. |

OTHER PUBLICATIONS

International Search Report dated Dec. 24, 2007.

*Primary Examiner* — Brent T Page
(74) *Attorney, Agent, or Firm* — Rothwell, Figg, Ernst & Manbeck, P.C.

(57) ABSTRACT

Provided is a method for producing a target protein via cultivation of transgenic plant cells comprising a promoter capable of expressing the protein under sugar-free conditions in the response to the depletion of sugar and a gene encoding the target protein, without exchange of a cell growth medium with a sugar-depleted medium comprising the addition of an amino acid mixture to the sugar-rich medium used to grow the plant cells.

13 Claims, 6 Drawing Sheets

METHOD FOR PRODUCING TARGET PROTEINS USING AMINO ACIDS AND PYRUVIC ACIDS IN CULTURE OF PLANT CELLS

CROSS REFERENCE TO RELATED APPLICATIONS

This application is a 35 USC §371 National Phase Entry Application from PCT/KR2007/004543, filed Sep. 19, 2007, and designating the United States. This application claims priority under 35 U.S.C. §119 based on Korean Patent Application No. 10-2006-0093112 filed Sep. 25, 2006 and Korean Patent Application No. 10-2007-0095146 filed Sep. 19, 2007, which are incorporated herein in their entireties.

TECHNICAL FIELD

The present invention relates to a method for producing a target protein via cultivation of transgenic plant cells comprising a promoter capable of expressing the protein under sugar-free conditions or in response to the depletion of sugar and a gene encoding the target protein, without exchange of a cell growth medium with a sugar-depleted medium.

BACKGROUND ART

With advanced plant biotechnology, a number of attempts have been actively made to produce high-value added beneficial proteins through large-scale cultivation of plant cells. Due to economical superiority resulting from inexpensive medium components, and easy production, isolation and purification of desired proteins, such plant cell culture-based production systems are receiving a great deal of attention as a substitute production system for medicinal proteins such as cytokines, growth factors and immunomodulators that have been produced by use of conventional microbial or animal cell culture (Miele, L., Trends Biotechnol., 15: 45-50, 1997; Doran, P. M., Curr. Opin. Biotechnol., 11: 199-204, 2000). Further, production of recombinant proteins via plant cell culture involves, unlike prokaryotic cells such as *E. coli*, a post-translational modification process almost similar to that exhibited by animal cells. Thus, it is easy to maintain biological activities of proteins thus prepared and it is also advantageous in view of safety, due to the decreased risk of incorporation of viruses or pathogenic bacteria fatal to humans, as compared to the animal cell culture utilizing sera.

However, there are still problems that have yet to be solved, such as slow cell growth of plant cell culture systems and lower expression rates of proteins than in microbial or animal cell culture systems, and various difficulties associated with realization of mass production processes. In addition, there is an urgent need for establishment of a plant cell cultivation method which is capable of achieving high concentration and large-scale cell culture via improvements of the culture processes.

When a promoter that expresses a protein under sugar-free conditions or in response to the depletion of sugar is employed in production of recombinant proteins using plant cells, the target protein is produced through two stages, e.g. a cell growth stage in which cells are allowed to grow in a sugar-rich medium, and a protein production stage in which the target recombinant protein is expressed in sugar-depleted production medium (Simmons C R, et al., Biotechnol. Bioeng., 38:545-551, 1991; and Karrer EE., et al., Plant J., 2:517-523, 1992).

However, the above-mentioned culture method suffers from various disadvantages and problems, such as an essential need for exchange of growth medium with sugar-free production media in conjunction with the risk of medium contamination, difficulty associated with application of a medium exchange process when scaling up a bioreactor, and increased production costs due to dual use of growth media and production media. Further, cell disruption may be caused by an imbalance in the osmotic pressure of cells which takes place under sugar-deficient conditions. In previous studies, addition of glucose at a low concentration during the protein expression phase has been proposed to solve such a problem associated with the osmotic imbalance. Unfortunately, the addition of glucose may result in functional suppression of promoters such as amylase promoters used in this expression system.

DISCLOSURE OF THE INVENTION

Technical Problem

As a result of a variety of extensive and intensive studies and experiments to develop a method for industrial large-scale production of a recombinant protein via cultivation of transgenic plant cells harboring a promoter capable of expressing a protein under sugar-free conditions or in response to the depletion of sugar, the inventors of the present invention have discovered that spontaneous induction of sugar depletion in a culture medium via feeding of an amino acid mixture can lead to low-cost mass production of proteins without medium exchange, and osmotic imbalance and cell death, resulting from spontaneous sugar depletion following addition of the amino acid mixture, can be arrested by addition of pyruvic acid. The present invention has been completed based on these findings.

Therefore, the present invention has been made in view of the above problems, and it is an object of the present invention to provide a method for industrial large-scale production of a target protein via cultivation of transgenic plant cells comprising a promoter capable of expressing the protein under sugar-free conditions or in response to the depletion of sugar and a gene encoding the target protein, without exchange of a cell growth medium with a sugar-depleted medium. The production method includes 1) a cell growth step of plant cells where the transgenic plant cells are cultured in a sugar-rich medium; and 2) an expression step of a target protein where the transgenic plant cells are cultured with addition of an amino acid mixture to the culture of Step 1, without exchange of a cell growth medium with a sugar-depleted medium.

Technical Solution

In accordance with an aspect of the present invention, the above and other objects can be accomplished by the provision of a method for producing a target protein via cultivation of transgenic plant cells containing a promoter capable of expressing the protein under sugar-free conditions or in response to the depletion of sugar and a gene encoding the target protein, comprising:

1) culturing the transgenic plant cells in a sugar-rich medium to grow plant cells; and 2) culturing the transgenic plant cells with addition of an amino acid mixture to the culture of Step 1 without exchange of a cell growth medium with a sugar-depleted medium, thereby expressing a target protein.

Best Mode

The present invention is directed to a method for producing a target protein via cultivation of transgenic plant cells containing a promoter capable of expressing the protein under sugar-free conditions or in response to the depletion of sugar and a gene encoding the target protein, comprising: 1) culturing transgenic plant cells in a sugar-rich medium to grow plant cells; and 2) culturing the transgenic plant cells with addition of an amino acid mixture to the culture of Step 1 without exchange of a cell growth medium with a sugar-depleted medium, thereby expressing a target protein.

In order to achieve the production of the target protein in the plant cells harboring a promoter that expresses the protein under sugar-free conditions or in response to the depletion of sugar, growth of the plant cells should be carried out in the sugar-rich medium whereas expression of the target protein should be carried out in the sugar-depleted medium. However, according to the method of the present invention, upon cultivation of the plant cells containing a promoter that can induce expression of the protein under sugar-starvation conditions, addition of an amino acid mixture can result in expression of the target protein even without exchange of a cell culture medium with a sugar-depleted medium, in conjunction with increased dry cell weight as well as increased production yield of the target protein.

In an embodiment of the present invention, cultivation of the transgenic plant cells may be carried out by fed-batch culture.

As used herein, the term "fed-batch culture" refers to a culture method involving a continuous or intermittent supply of media without exchange or removal of the culture media, unlike batch culture which involves closed cultivation of cells in a given medium without supplementation of nutrient broth or nutrients. The fed-batch culture is advantageous in that it is possible to actively control a substrate concentration in the culture medium as required.

As can be confirmed from Example 3 which will be illustrated hereinafter, the production yield of the target protein can be significantly enhanced by culturing of plant cells through the fed-batch culture which is accompanied by no potential risk of contamination during medium exchange and no need for dual use of growth media and production media, and addition of an amino acid mixture during the culturing process.

When it is desired to carry out the fed-batch culture, a culture medium, a culture temperature, a culture method (agitation) and the like may be appropriately adjusted depending upon kinds of plant cells for suspension culture.

In the present invention, the amino acid mixture may be a mixture of two or more amino acids selected from the group consisting of glycine, L-glutamine, L-aspartic acid, L-arginine, tryptophan, alanine, proline and asparagine.

In one embodiment of the present invention, the amino acid mixture is a mixture of glycine, L-glutamine, L-aspartic acid and L-arginine.

In the fed-batch culture, nutrients are concentrated and then supplied in order to adjust a concentration of the nutrients to a desired level while not affecting a volume inside a bioreactor.

In one embodiment of the present invention, the amino acid mixture is added to elicit protein expression of transgenic plant cells. For this purpose, 10-, 20-, and 30-fold concentrated mixture of amino acids (glycine 1.0 mM, L-glutamine 6.0 mM, L-aspartic acid 2.0 mM, and L-arginine 1.3 mM) contained in an AA medium are each dissolved in sugar-free media which were then added to culture media. Here, an addition amount of the medium is adjusted such that a final concentration of the amino acid mixture in the culture medium is 1-, 2- and 3-fold the concentration of amino acids contained in the AA medium. In this manner, the concentration of the amino acid mixture to maximize the protein expression by cultivation of transgenic plant cells was estimated.

The final concentration of the amino acid mixture in the culture medium necessary for induction of protein expression through culturing of transgenic plant cells may be 1.0 to 5.0 mM glycine, 6.0 to 30 mM L-glutamine, 2.0 to 10 mM L-aspartic acid, and 1.3 to 6.5 mM L-arginine.

In the present invention, the amino acid mixture may be added to a plateau phase of transgenic plant cells.

Culture step of the plant cells is divided into a lag phase, an exponential (logarithmic) growth phase, a plateau phase (decelerating growth phase), and a stationary phase (death phase). Generally, the exponential growth phase corresponds to a period of from Days 3 to 7 after the start of culture, the plateau phase corresponds to a period of from Days 7 to 11 after the start of culture, and the stationary phase is after 11 days. In the following Examples, the amino acid mixture was added to the exponential growth phase (Day 3 of culture), the plateau phase (Day 7 of culture), and the stationary phase (Day 11 of culture), respectively, and the dry cell weight and the expression level of target proteins are examined. According to the embodiment of the present invention, addition of the amino acid mixture to the exponential growth phase leads to a more rapid decrease in the dry cell weight. Twice addition of the amino acid mixture to both the exponential growth phase and the plateau phase exhibits a lower dry cell weight, as compared to addition of the amino acid mixture only to the plateau phase. Further, addition of the amino acid mixture to the stationary phase results in a decreased expression level of the target protein. Therefore, the amino acid mixture is preferably added to the plateau phase of the plant cells, but not to the exponential growth phase.

In the production method of the target protein in accordance with the present invention, Step 2 may further include addition of pyruvic acid.

Addition of the amino acid mixture results in earlier depletion of sugars in the culture medium while producing proteins. Sugar depletion in the culture is accompanied by initiation of protein expression simultaneously with onset of a cell death phase. Upon entrance of cells into the death phase, the production of the protein is halted or proteolysis is caused by extracellularly-excreted proteases or cell debris. However, as can be seen from Example 4 which will follow hereinafter, a further addition of pyruvic acid during expression of the target protein brings about retardation of cell death which may occur due to sugar depletion, and consequently a significantly increased protein expression level. According to the embodiment of the present invention, a further addition of pyruvic acid (Example 4) exhibits about 2.4-fold increased productivity of the target protein, as compared to expression-induced culture process (Example 3) with simple addition of the amino acid mixture. According to the embodiment of the present invention, a concentration of added pyruvic acid may be in a range of 20 mM to 80 mM.

In the present invention, the cell culture may be carried out in a bioreactor.

In an embodiment of the present invention, the bioreactor is a reactor suitable for plant cell culture, which, for this purpose, may be equipped with a hollow-paddle impeller, a disk-type gas sparger and a sampling port having a moderate size suited for collection of plant cells.

As used herein, the term "promoter capable of expressing the protein under sugar-free conditions or in response to the depletion of sugar" may encompass any promoter that is operated to express proteins under sugar-depleted or sugar-free conditions. Genes having a promoter that regulates expression of proteins in response to the depletion of sugar are known in the art. For example, mention may be made of photosynthetic genes in maize mesophyll protoplasts, Suc synthase (Sh1) gene in maize root tips, malate synthase (MS) gene and isocitrate lyase gene of cucumber, and α-amylase genes in rice suspension cells and germinating embryos (Yu S-M, Plant Physiol., 1999, pp. 687-693). In an embodiment of the present invention, the sugar starvation-inducible promoter may be a rice α-amylase RAmy3D promoter. Upon comparing with tobacco cell lines BY-2 and NT-1, the RAmy3D promoter, which belongs to a rice α-amylase gene family (αAmy3), provides significantly remarkable productivity, despite intrinsic characteristics and relatively low growth rates of rice cell lines. Therefore, utilization of the aforesaid RAmy3D promoter enables production of desired proteins on an industrial scale.

In the present invention, the target protein may be any recombinant protein. Therefore, examples of the target protein may include any recombinant protein which needs expression in plant cells at lower production costs and higher production efficiency, as compared to microbial cell culture or animal cell culture. There is no particular limit to kinds of the target protein, even though a human cytotoxic T lymphocyte antigen 4 Immunoglobulin (hereinafter, referred to as "hCTLA4Ig") is used as the target protein in an embodiment of the present invention.

As used herein, the term "plant cells" is intended to encompass any transgenic plant cells comprising a promoter capable of expressing the protein under sugar-free conditions or in response to the depletion of sugar, as mentioned above, and a gene encoding a certain target protein. Examples of the plant cells may include, but are not limited to, rice (*Oryza Sativa* L. cv. Dongjin), tobacco (*Nicotiana tabacum*), maize (*Zea mays*), soybean (*Glycine max*), wheat (*Triticum aestivum*), tomato (*Lycopersicon esculentum*), rape (*Brassica napus*), and potato (*Solanum tuberosum*). In the embodiment of the present invention, rice cells are used as the plant cells.

The transgenic rice cells may be a cell line selected from the group consisting of Accession Numbers KCTC 10618BP, KCTC 10767BP and KCTC 10768BP.

In one embodiment of the present invention, a rice cell line transformed to express human CTLA4Ig (cytotoxic T lymphocyte antigen 4 Immunoglobulin), *Oryza Sativa* (Accession No. KCTC 10618BP) is used as the transgenic plant cell. Preparation of the aforesaid transgenic rice cell line is detailed in Korean Patent Application Publication No. 2005-0112715 A1, the disclosure of which is hereby incorporated by reference in its entirety. The transgenic rice cell lines under Accession No. KCTC 10767BP and Accession No. KCTC 10768BP may also be employed as transgenic plant cells of the present invention. Details for preparation of these cell lines can be found in PCT/KR2005/001582, the disclosure of which is also hereby incorporated by reference in its entirety. Accession No. KCTC 10618BP, KCTC 10767BP and KCTC10768BP are all transgenic rice cell lines adapted to express CTLA4Ig, each recombinant vector of which is pMYN409, pMYN413, and pMYN414. pMYN413 and pMYN414 comprise a DNA sequence with modification of a portion of hCTLA4Ig fusion protein-coding gene contained in pMYN409.

The aforementioned transgenic rice cell lines comprises a RAmy3D promoter of rice α-amylase as an expression system, wherein a target protein is induced by a signal sequence of rice α-amylase upon sugar starvation of the medium and is then secreted into a culture medium. Therefore, after suspension culture of the rice cell lines in a growth medium, addition of an amino acid mixture capable of inducing expression of the target protein can bring about high-efficiency protein expression via the fed-batch culture without exchange of culture media.

ADVANTAGEOUS EFFECTS

As will be illustrated hereinafter, a method of the present invention enables commercial-scale production of recombinant proteins via establishment of optimized culture conditions by addition of an amino acid mixture to induce protein expression without exchange of a cell growth medium with a sugar-free medium, and addition of pyruvic acid during the induction period of protein expression to thereby enhance the production yield of target proteins.

MODE FOR INVENTION

Figure 1:
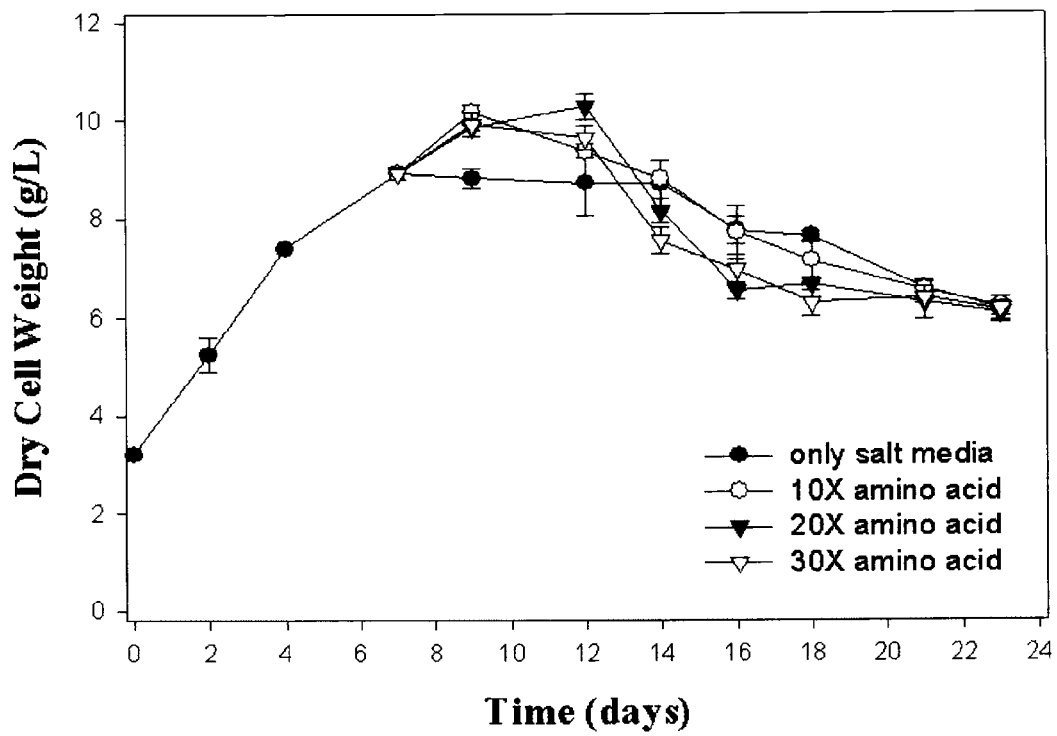
FIG. 1 is a graph showing time-course changes in dry cell weights after addition of varying concentrations of an amino acid mixture to suspension cultures of plant cells.

Now, preferred embodiments of the present invention will be described in more detail, such that those skilled in the art can easily practice the present invention. These and other objects, advantages and features of the present invention will become apparent from the detailed embodiments given below which are made in conjunction with the following Examples. The present invention may be embodied in different forms and should not be misconstrued as being limited to the embodiments set forth herein, and those skilled in the art will appreciate that various modifications, additions and substitutions are possible without departing from the scope and spirit of the invention as disclosed in the accompanying claims. Therefore, it should be understood that the embodiments disclosed herein are provided only for illustrating the present invention and should not be construed as limiting the scope and spirit of the present invention.

EXAMPLES

Pre-culture of Transgenic Rice Cells

Transgenic rice cell line KCTC 10618BP used in this Example is a transgenic plant cell which comprises a RAmy 3D promoter of rice α-amylase and expresses human CTLA4Ig (rCTLA4Ig). An important property of this expression system is in that a target protein is induced by a signal sequence of rice α-amylase upon sugar starvation of the medium and is then secreted into a culture medium.

For cell culture according to following Examples 1 to 4, proliferation of transgenic rice cells is necessary via pre-culture.

A sucrose-containing AA medium was used to grow cells in this pre-culture step. The AA medium consists of amino acids (glycine, L-glutamine, L-aspartic acid, L-arginine, etc), inorganic acids and hormones (Thompson et al. 1986; and Terashima et al. 1999). After preparation of the medium was complete, an acidity of the AA medium was adjusted to a pH of 5.8 using NaOH.

150 mL of AA medium was aliquoted into a 500 mL flask into which the transgenic rice cells were then suspended at a 10% fresh cell density. Thereafter, the cells were pre-cultured in a shaking incubator at 110 rpm and 28° C. under dark conditions. For maintenance of the cell line, pre-culture of cells was carried out for 7 days with exchange of the culture medium with a sucrose-containing AA medium at an interval of 10 days.

Example 1

Effects of Amino Acid Mixture with Varying Concentrations on Expression of Target Protein 30 mL of a sucrose-containing AA medium was aliquoted into a 100 mL flask, and each 1 g of the pre-cultured transgenic suspension cells was inoculated into the media, followed by cultivation for 7 days to undergo growth stages of rice cells. In order to examine changes in target protein expression levels and cell mass with or without addition of the amino acid mixture during the expression period of target protein and with varying concentrations of the amino acid mixture, 3 mL of a sugar-free medium (Control) and each 3 mL of AA media containing 10-, 20-, and 30-fold concentrated amino acids (glycine 1.0 mM, L-glutamine 6.0 mM, L-aspartic acid 2.0 mM, and L-arginine 1.3 mM) were added to the cell cultures which passed through the growth stages, without replacement of the culture medium with a sugar-depleted medium. A final concentration of the amino acid mixture in the culture medium was 1-, 2- and 3-fold as the concentration of amino acids contained in the AA medium. Samples were collected throughout the culture period at intervals of 2 to 3 days.

Cell growth factors were observed through measurement of dry cell weight (DCW). Cell suspension samples were placed in a graduated cylinder and the volume of the settled cells was recorded after 10 min. The supernatant was filtered and frozen at −70° C. for subsequent analysis. To determine the dry cell weight, the cell suspension sample was filtered through a paper filter under vacuum to remove the supernatant and then washed with distilled water. The dry cell weight was then estimated after drying at 50 to 60° C. for 2 to 3 days. Sugar values for sucrose, glucose and fructose were measured using a refractive index (RI) detector, and only the total sugar concentrations were given.

An expression level of rCTLA4Ig was determined by ELISA. The supernatant in the culture was taken in a microtube and frozen at −70° C. until use. Plates were coated with 1 μg/mL of anti-CTLA4 antibodies, followed by reaction at 37° C. for 2 hours. Each well was loaded with samples or human standard Ig in a concentration ranging from 11.6 to 0.09 ng/mL, in two-fold serial dilutions. Peroxidase-labeled anti-human Ig antibody was used as the detection antibody. After color development using a 2,2'-azino-bis(3-ethylbenzthiazoline-6-sulfonic acid) (ABTS) peroxidase substrate, an absorbance was measured at a wavelength of 405 nm using a microplate reader.

Figure 2:
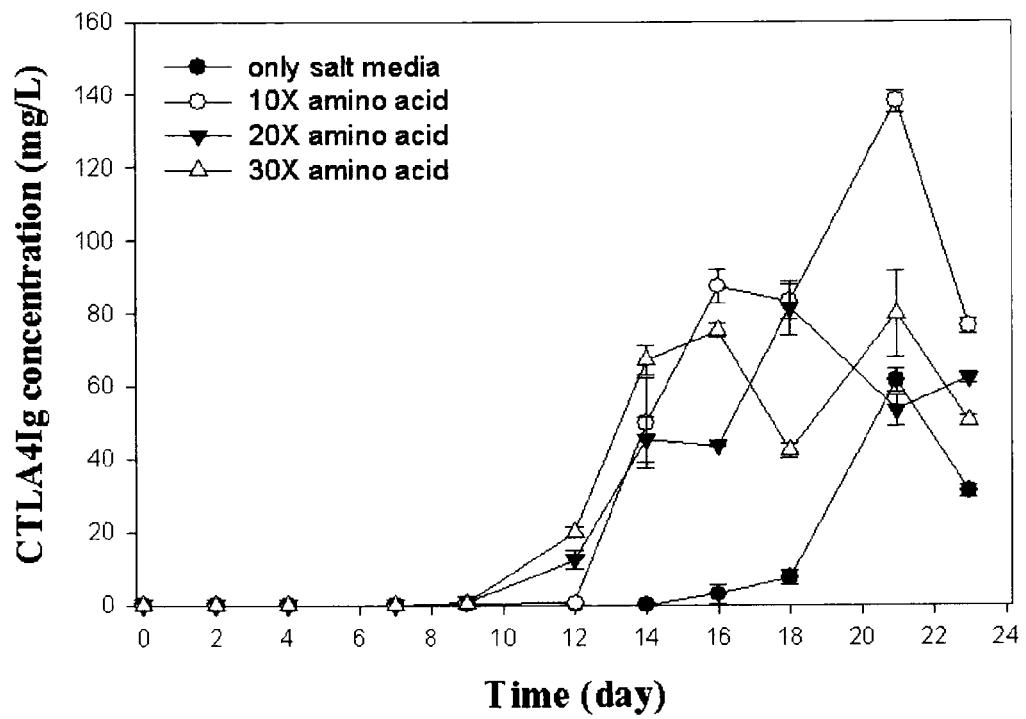
FIG. 2 is a graph showing time-course changes in human CTLA4Ig expression levels.

Dry cell weights (DCW) and amounts of hCTLA4Ig protein in the culture as determined above are shown in graphs of FIGS. 1 and 2, respectively.

FIGS. 1 and 2 exhibit effects of varying concentrations of an amino acid mixture on protein expression. FIG. 1 shows changes in dry cell weights upon addition of an amino acid mixture at different concentrations, and FIG. 2 is a graph showing changes in rCTLA4Ig expression levels upon addition of an amino acid mixture at different concentrations. As shown in FIGS. 1 and 2, addition of a sugar-free medium exhibited no further increase in the dry cell weight after 7 days of culture, as compared to a culture flask to which a medium supplemented with an amino acid mixture was added. On Day 21 of culture after addition of a sugar-free medium, 67.74±5.36 mg/L of the rCTLA4Ig protein was produced.

Addition of the amino acid mixture resulted in an increase in the dry cell weight, which lasted for up to about 5 days. A higher concentration of the amino acid mixture resulted in a decrease in the dry cell weight over time. Further, more rapid production of the rCTLA4Ig protein was initiated with the addition of the amino acid mixture, and addition of 10-fold concentrated amino acid mixture exhibited the highest production of the rCTLA4Ig protein of 138.11±2.95 mg/L on Day 21 of culture, which is an about 2-fold increase as compared to the flask culture with no addition of the amino acid mixture. Increasing concentrations of the amino acid mixture showed substantially no difference in the dry cell weight, but protein expression levels were lower or decreased more rapidly. Therefore, it is considered that a high concentration of amino acid exhibits effects on the cell viability and stability of the rCTLA4Ig protein.

In conclusion, in order to increase expression of the target protein, it can be seen that amino acids in the AA medium used in the cell growth step are preferably added as a 10-fold concentrated amino acid mixture at an optimum concentration.

Example 2

Effects of Amino Acid Mixture Addition at Varying Time Points on Expression of Target Protein Based on the results of Example 1, an optimum addition concentration of an amino acid mixture was determined to be 10-fold that of amino acids in the AA medium used in the cell growth stage, and reasonable addition time points and the number of times of addition were given consideration. The addition time point of the amino acid mixture was divided into 3 phases taking into consideration a growth curve for typical batch culture, and the 10-fold concentrated amino acid mixture was added to an exponential growth phase (on Day 3 of culture), a plateau phase (on Day 7 of culture), and a stationary phase (on Day 11 of culture), respectively. The number of times of addition consisted of once on Day 3, 7 or 11, twice on Days 3 and 7, and three times on Days 3, 7 and 11.

Figure 3:
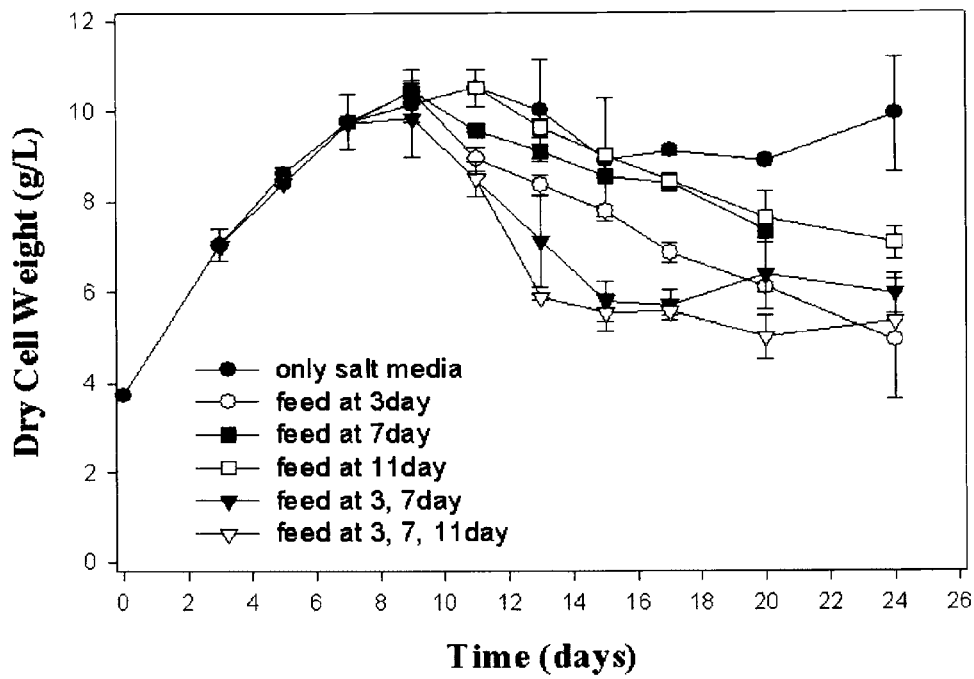
FIG. 3 is a graph showing time-course changes in dry cell weights after addition of an amino acid mixture at various time points to suspension cultures of plant cells.
Figure 4:
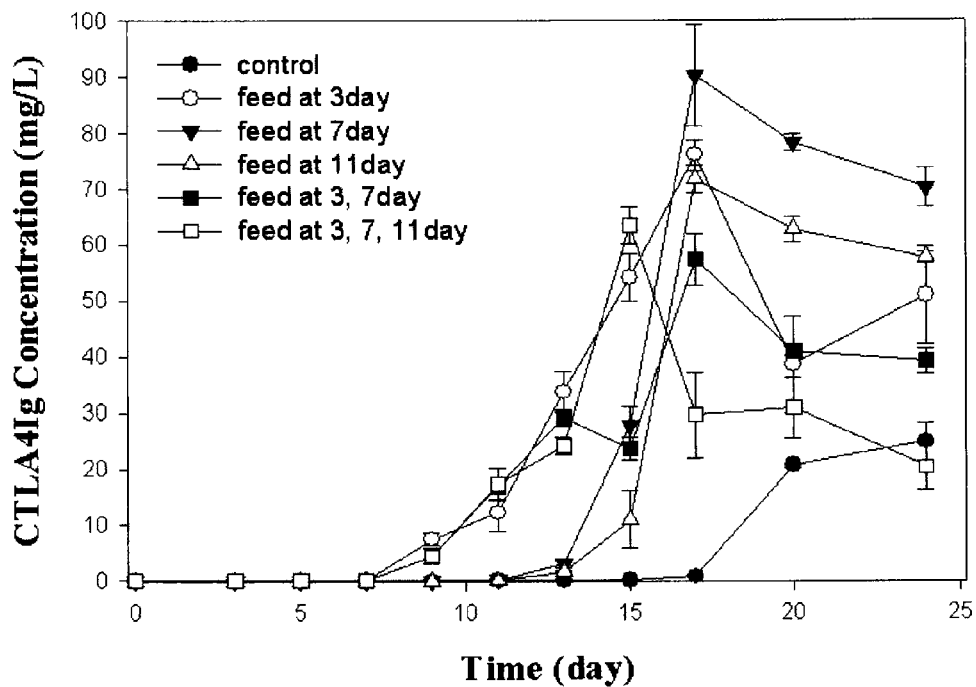
FIG. 4 is a graph showing time-course changes in human CTLA4Ig expression levels.
Figure 5:
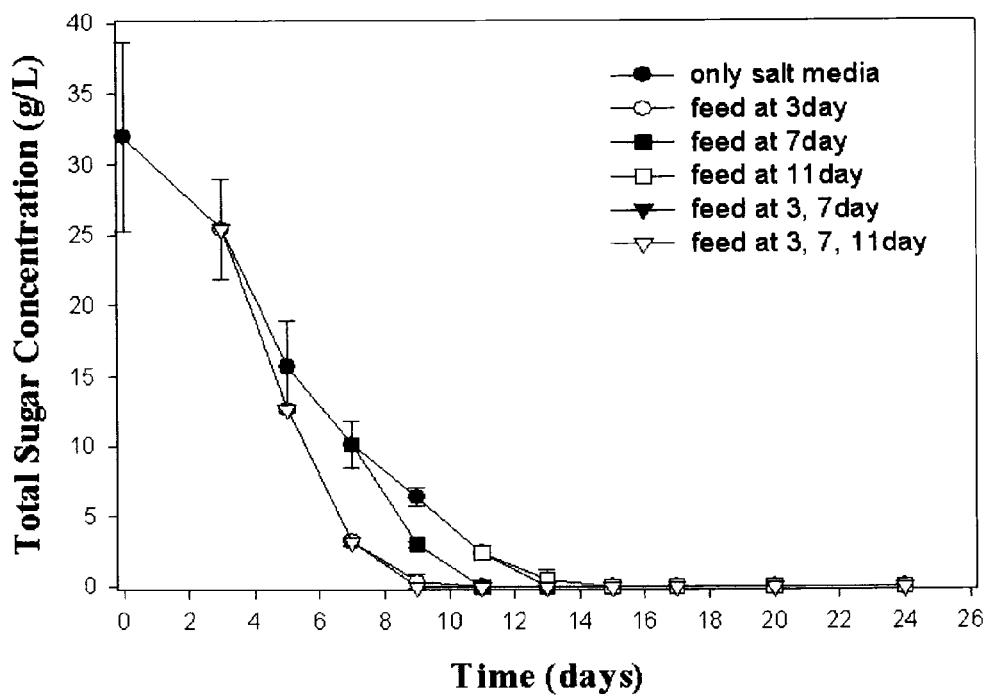
FIG. 5 is a graph showing time-course changes in sugar concentrations.

The results thus obtained are given in FIGS. 3 to 5. FIG. 3 is a graph showing changes in dry cell weights upon addition of an amino acid mixture at various time points, FIG. 4 is a graph showing changes in rCTLA4Ig expression levels upon addition of an amino acid mixture at various time points, and FIG. 5 is a graph showing changes in total sugar concentrations upon addition of an amino acid mixture at various time points.

As shown in FIG. 3, cells with addition of the amino acid mixture on Day 3 of culture exhibited a more rapid decrease in the dry cell weight, as compared to cells without addition of the amino acid mixture or with addition of the amino acid mixture on Days 7 and 11 of culture. Further, the dry cell weight was lower in the group to which amino acids were added twice or three times, as compared to the group with addition of amino acids once. From these results, it can be seen that addition of the amino acid mixture on Day 3 of culture, corresponding to the exponential growth phase where cell actively grows, exhibits adverse effects on cell growth. In addition, it can also be seen that a single addition of the amino acid mixture is effective for cell growth.

As shown in FIG. 4, expression of the rCTLA4Ig protein was initiated about 5 days after an addition time point of the amino acid mixture, and an earlier time point of addition resulted in more rapid production of the rCTLA4Ig protein. However, lower or rapidly decreasing expression of the rCTLA4Ig protein was also observed with earlier addition of the amino acid mixture. Further, the group with addition of the amino acid mixture on Day 11 of culture corresponding to the stationary phase exhibited a lower expression level of the target protein, as compared to the group with addition of the amino acid mixture on Day 7 of culture corresponding to the plateau phase (decelerating growth phase). From these results, it can be seen that the optimum addition time point of the amino acid mixture is Day 7 of culture corresponding to the plateau phase (decelerating growth phase) and the number of times of addition is preferably once. An increasing number of addition times resulted in a more rapid decrease in the expression of the target protein. These results were similar to those observed in Example 1. The group with a single addition of the amino acid mixture on Day 7 of culture showed an about 3-fold further increase in the protein expression level, as compared to the group without addition of the amino acid mixture.

As shown in FIG. 5, it can be seen that a sugar consumption rate further increases during addition of the amino acid mixture. It is therefore believed that the amino acid mixture serves as a nitrogen source for cell growth, which thereby increases consumption of a carbon source. Accordingly, it can be seen that the consumption of the carbon source, taking place on Day 3 of culture which corresponds to the exponential growth phase, exhibits adverse effects on cell growth or protein expression.

Therefore, it can be seen that the optimum addition condition to increase the protein expression is addition of the 10-fold concentrated amino acid mixture as a proper concentration on Day 7 of culture once.

Bioreactor Operation

In the following Comparison Example 1 and Example 3, cell culture was carried out in a bioreactor for large-scale culture of plant cells pre-cultured in a flask. The bioreactor operation commonly conducted in Comparison Example 1 and Example 3 is as follows.

The bioreactor that had been modified suitable for use with plant cell culture was used which is equipped with a hollow-paddle impeller, a disk-type gas sparger, and a sampling port having a moderate size suited for collection of plant cells. An inorganic salt medium was sterilized by autoclaving it within the bioreactor at 121° C. for 25 min. Various hormones and 10-fold concentrated amino acids that had been filtered through a 0.22-μm filter (Millipore, USA) were infused into the bioreactor together with the cells. After sterilization, flask-cultured cells were inoculated at a 10% fresh cell weight volume (FCWV). The culture temperature was maintained at 28° C. To maintain the dissolved oxygen (DO) level at greater than 20%, oxygen was mixed with air and supplied into the bioreactor. An aeration rate was set to a rate of 0.5 L/min for air, and at a rate intermittently between 0.1 mL/min and 100 mL/min for oxygen. The bioreactor culture was carried out under alternating fluorescent light illumination conditions and dark conditions. Culture conditions of the growth stage were similar to those of Examples 1 and 2. Samples of 10 to 15 mL were collected aseptically through the sampling port at an interval of 2 to 3 days.

Comparison Example 1

Effects of Sugar Depletion on Protein Expression and Cell Growth in Batch Culture The batch culture was carried out in a 7-L bioreactor and effects of sugar depletion on protein expression and cell growth were examined.

Exchange of growth culture medium of plant cells with a sugar-free medium is essential in operation of a RAmy3D promoter for expression of rCTLA4Ig. To induce expression of rCTLA4Ig in the batch culture, a peristaltic pump was used to exchange the culture medium in the bioreactor with AA medium that did not contain any sugar (AAS(−) medium) and had been sterilized by filtering through a 0.22-μm filter. A mesh line with a pore retention size of 20 μm was separately positioned at the bottom of the bioreactor to filter the medium while retaining the cells inside.

Figure 6:
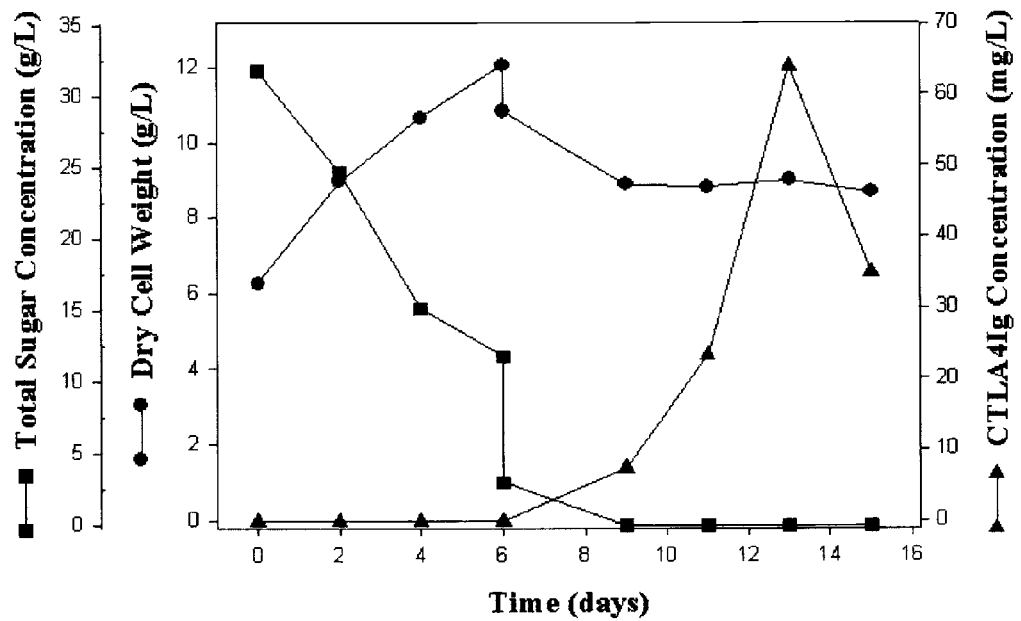
FIG. 6 is a graph showing time-course changes in dry cell weights, human CTLA4Ig expression levels and sugar concentrations, upon exchange of a culture medium with an expression-inducing medium in plant cell culture using a 7-L bioreactor.

As shown in FIG. 6, the culture medium was replaced with a sugar-free medium on Day 6 of culture, and the remaining sugar was completely consumed at an early stage of expression. 3 days after medium exchange, sugar was completely depleted with initiation of expression. Cell death is not rapid unlike the early stage of expression, and CTLA4Ig expression on Day 7 of expression reached a maximum level of 63.94 mg/L.

Example 3

Figure 7:
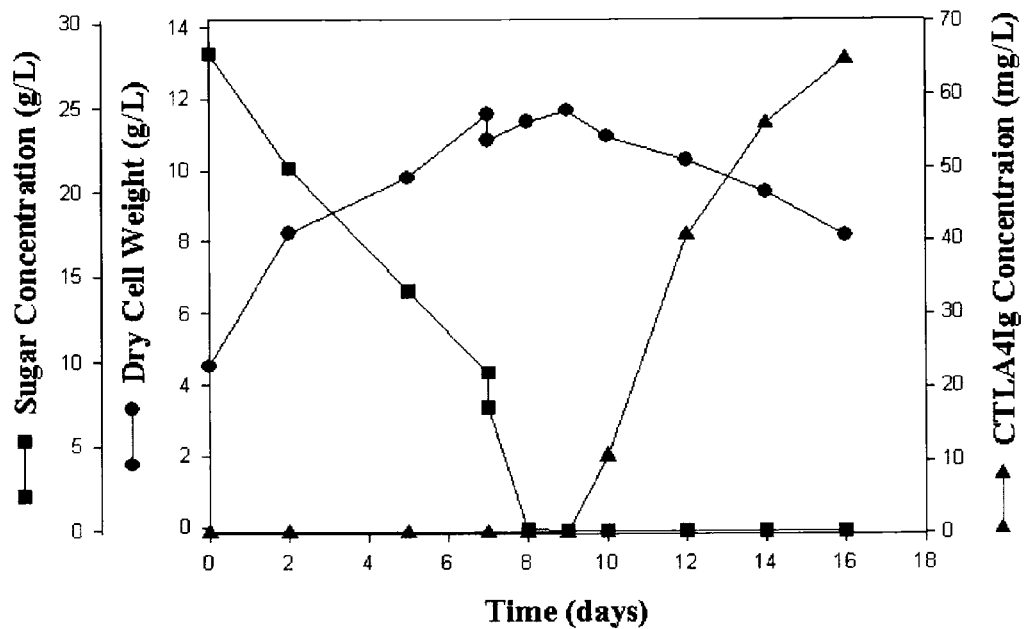
FIG. 7 is a graph showing time-course changes in dry cell weights, human CTLA4Ig expression levels and sugar concentrations, upon induction of expression without medium exchange in plant cell culture using a 7-L bioreactor.

Effects of Amino Acid Feeding on Protein Expression and Cell Growth in Fed-batch Culture Based on flask experiments performed in Examples 1 and 2, fed-batch culture without medium exchange in a 7-L bioreactor was carried out which involves feeding of an amino acid mixture under the state where sugar remains. In order to feed the amino acid mixture without medium exchange, amino acids were 10-fold concentrated, dissolved in an inorganic salt and hormone medium, and infused into the culture medium, taking into consideration the total volume. As shown in FIG. 7, amino acid feeding was made on Day 7 of culture corresponding to the exponential growth phase, and the dry cell weight (DCW) was 11.58 g/L. The sugar concentration at the time of amino acid feeding was similar to the sugar concentration obtained after feeding of amino acids, because exchange of the culture medium with a sugar-free medium was not made. The remaining glucose and fructose were completely consumed at the early stage of expression. After feeding of amino acids, the dry cell weight was 10.84 g/L. After feeding of amino acids, cell growth increased up to 11.67 g/L on Day 2 of expression. This is due to less effects of osmotic pressure. Upon entering the expression stage, the cell weight decreases. This is thought to be due to decreased inorganic salts and hormones in the culture, unlike in the batch culture involving replacement of the culture medium with a fresh medium, as well as due to inhibitory actions by several kinds of proteases and cell debris produced during various other expression stages. Protein expression began to increase on Day 2 of expression, and CTLA4Ig expression reached a maximum level of 64.8 mg/L on Day 9 of expression.

Figure 8:
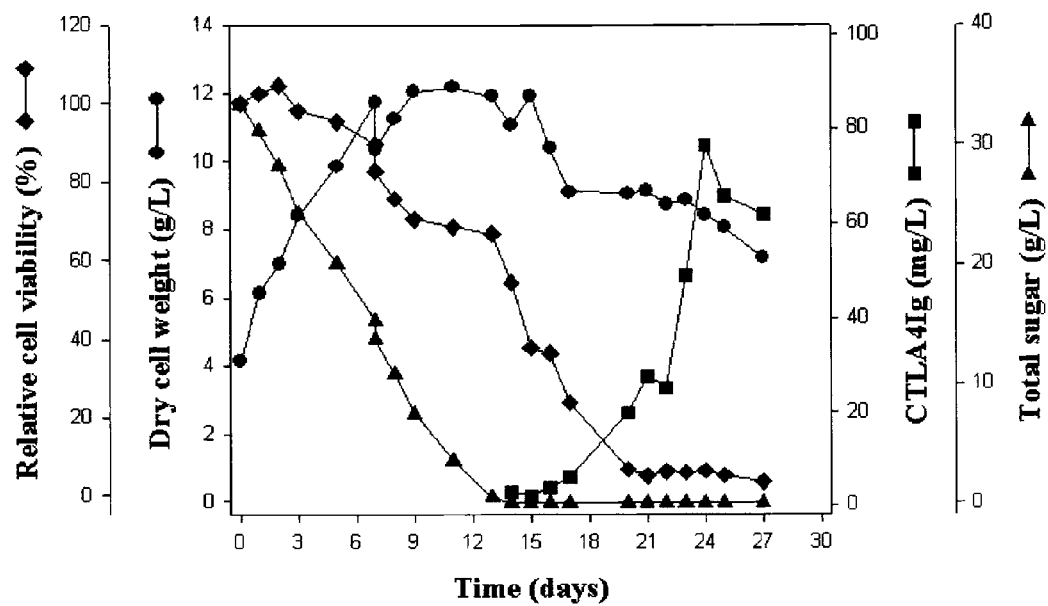
FIG. 8 is a graph showing time-course changes in dry cell weights, human CTLA4Ig expression levels, sugar concentrations and cell viability, when induction of expression without medium exchange is applied to a 15-L bioreactor.

Through scale-up of a 7-L bioreactor, the reproducibility of CTLA4Ig expression due to amino acid feeding was examined in a 15-L bioreactor. The results thus obtained are shown in FIG. 8. Expression of CTLA4Ig was initiated on Day 5 at which time sugar is completely depleted after amino acid feeding, and then increased to a maximum level of up to 76.5 mg/L on Day 12 of expression, which is an about 1.2-fold increase as compared to the batch culture with medium exchange. The scale-up of culture resulted in a decreased cell death rate, and the cell mass was maintained constantly during the plateau phase, which was thereby evaluated to bring about an increase in the expression amount of the protein.

Upon comparing expression levels of the target protein between different types of cultures, based on the results of Comparison Example 1 and Example 3,7-L batch culture produced about 60 mg of CTLA4Ig in 1.67 L of a total harvest volume on Day 9 of expression induction, and 7-L fed-batch culture produced about 120 mg of CTLA4Ig in 1.8 L of the total harvest volume on Day 9 of expression induction. The fed-batch culture in a 15-L bioreactor exhibited a maximum CTLA4Ig expression level of 76.5 mg/L (on Day 24 of culture) which is about 1.2-fold higher than that of 7-L fed-batch culture, and produced about 443.7 mg of CTLA4Ig in 5.8 L of the total harvest volume on Day 17 of expression induction.

Table 1 below shows the production yield of hCTLA4Ig/DCW/final harvest volume, depending upon different types of cultures in the bioreactor.

TABLE 1

| | CTLA4-Ig maximum productivity | | | |
|---|---|---|---|---|
| Type | texpr (days) | Maximum hCTLA4Ig (mg/L) | Specific content (mg/g DCW) | Volumetric productivity* (mg/L/day) |
| Batch (7-L) | 7 | 63.9 | 7.1 | 5.1 |
| Fed-batch(7-L) | 9 | 64.8 | 8.0 | 4.2 |
| Fed-batch(15-L) | 12 | 76.5 | 9.1 | 4.7 |

*Volumetric productivity = {rCTLA4Ig (mg/L) × Harvest volume (L)}/{working volume *(L) × texpress (days)}
**Harvest volumes: Batch (7-L); 1.67 L, fed-batch (7-L); 1.8 L, and fed-batch (15-L); 5.80 L
***Working volume (in the induction phase): Batch (7-L); 3.0 L, fed-batch (7-L); 3.1 L, fed-batch (15-L); 7.56 L Experimental Example 1

Expression Profiles of CTLA4Ig with Varying Culture Periods

Expression profiles of CTLA4Ig produced in the 7-L fed-batch culture with respect to varying culture periods of time were confirmed using SDS-PAGE (FIG. 9A) and Western blot (FIG. 9B).

SDS-PAGE was performed using 10% Tris-glycine gel (Invitrogen, USA). A molecular weight of the protein was confirmed by staining of the gel with Coomassie Blue R (Sigma). In order to confirm the protein molecular weight via Western blot analysis, SDS-PAGE was followed by blotting on a PVDF membrane using an electroblotting module (Mini-Blot cell, Invitrogen). The membrane was reacted with monoclonal anti-hCTLA4 (CD152) antibodies (from mouse, R&D) as the primary antibody. Peroxidase-labeled anti-mouse IgG (from goat, KPL Inc., USA) was used as the secondary antibody. After reaction of antibodies with a substrate, washing of reactants with distilled water was carried out to terminate the reaction. The reaction with specific antibodies confirmed the expression of the hCTLA4Ig fusion protein having a molecular weight of about 50 kDa.

Figure 9:
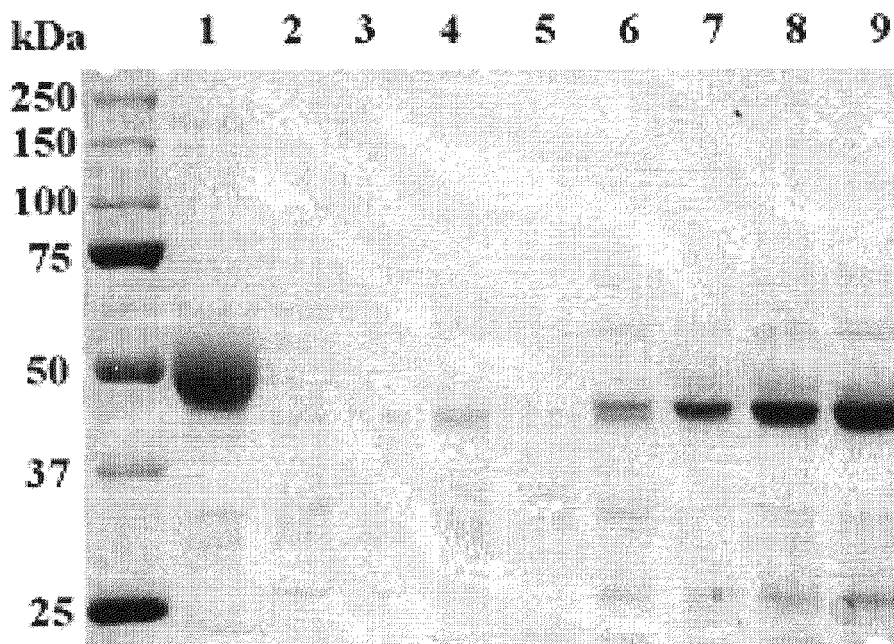
FIG. 9A is a photograph showing electrophoretic patterns of CTLA4Ig proteins taken at various culture periods, in fed-batch culture using a 7 L-bioreactor.
FIG. 9B is a photograph showing Western blot analysis of CTLA4Ig proteins.
Figure 9:

In FIG. 9, M represents a marker, e.g. pre-stain protein marker, and the rest of the lanes show samples of the hCTLA4Ig protein taken after induction by amino acids. Lane 1: animal-derived hCTLA4Ig standard (150 mg/L) (Control), Lane 2: 7 days of growth before addition of an amino acid mixture (0 mg/L); Lane 3: 7 days of growth immediately after addition of an amino acid mixture (0 mg/L); Lane 4: 8 days later (0.10 mg/L); Lane 5: 9 days later (0.0264 mg/L); Lane 6: 10 days later (10.55 mg/L); Lane 7: 12 days later (40.688 mg/L); Lane 8: 14 days later (56.025 mg/L); and Lane 9: 16 days later (64.8 mg/L). Based on the results of the SDS-PAGE analysis, the thick bands shown in Lanes 4 to 9 (approximately 45 kDa) were amylase bands, which did not react with anti-hCTLA4 antibody in the Western blot. In addition, the Western blot analysis indicated that the expression level of hCTLA4Ig as indicated by the immunoreactive band increases as the culture time increases. Furthermore, the immunoreactive band was not detected in samples during the growth period prior to the amino acid feeding, however, the immunoreactivity was confirmed 3 days after amino acids feeding.

Example 4

Effects of Pyruvic Acid Addition on Dry Cell Weight and CTLA4Ig Expression

Figure 10:
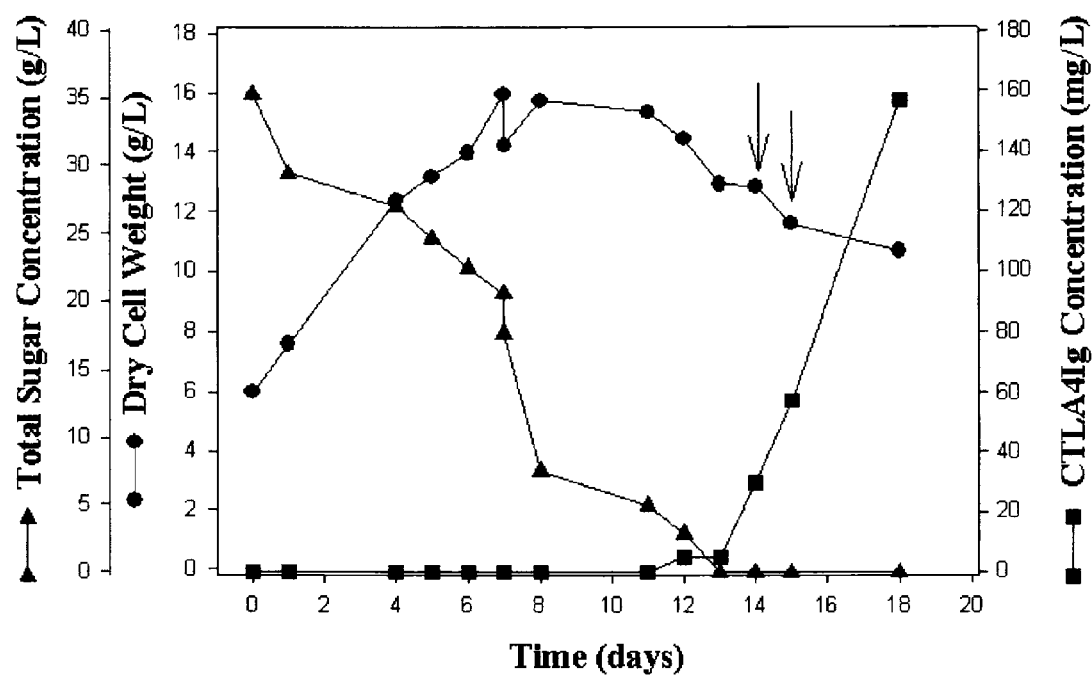
FIG. 10 is a graph showing time-course changes in sugar concentrations, dry cell weights and human CTLA4Ig expression levels, upon addition of pyruvic acid to plant cell cultures.

Based on the fed-batch culture (addition of amino acid mixture) method as shown in Example 3, a pyruvic acid addition experiment was carried out in a 7-L bioreactor. Cell growth stage and protein expression induction stage of plant cell culture were the same as in the fed-batch culture of Example 3. Addition of pyruvic acid was initiated on Day 14 of culture at which sugars in the culture are completely exhausted and therefore the protein expression increases. Here, pyruvic acid was added total of two times on Days 14 and 15 of culture (as indicated by the arrow in FIG. 10). To make a final concentration of 20 to 80 mM in the culture, pyruvic acid was dissolved in a sugar-free medium and added to the culture. The dry cell weight prior to addition of pyruvic acid was 12.83 g/L, whereas the dry cell weight on Day 18 of culture was 10.68 g/L. As a result, a delay rate of cell death was increased by about 15%, as compared to the fed-batch culture process with addition of an amino acid mixture and no addition of pyruvic acid. As shown in FIG. 10, the CTLA4Ig expression exhibited 4.9 mg/L on Day 12 of culture and then increased to a maximum level of up to 157.6 mg/L on Day 18 of culture.

What is claimed is:

1. A method for producing a target protein via cultivation of transgenic plant cells containing a promoter capable of expressing the protein under sugar-free conditions or in response to the depletion of sugar and a gene encoding the target protein, comprising:
   1) culturing the transgenic plant cells in a sugar-rich medium to grow plant cells; and
   2) culturing the transgenic plant cells with addition of an amino acid mixture to the culture of Step 1 without exchange of a cell growth medium with a sugar-depleted medium, thereby expressing a target protein.

2. The method according to claim 1, wherein cell culture is carried out by fed-batch culture.

3. The method according to claim 1, wherein the amino acid mixture is a mixture of two or more amino acids selected from the group consisting of glycine, L-glutamine, L-aspartic acid, L-arginine, tryptophan, alanine, proline and asparagine.

4. The method according to claim 3, wherein the amino acid mixture is a mixture of glycine, L-glutamine, L-aspartic acid and L-arginine.

5. The method according to claim 4, wherein the final concentration of the amino acid mixture in the culture medium is 1.0 to 5.0 mM glycine, 6.0 to 30 mM L-glutamine, 2.0 to 10 mM L-aspartic acid, and 1.3 to 6.5 mM L-arginine.

6. The method according to claim 1, wherein Step 2 includes addition of the amino acid mixture to a plateau phase of transgenic plant cells.

7. The method according to claim 1, wherein Step 2 further includes addition of pyruvic acid.

8. The method according to claim 7, wherein the final concentration of pyruvic acid in the culture medium is in the range of 20 mM to 80 mM.

9. The method according to claim 1, wherein the cell culture is carried out in a bioreactor.

10. The method according to claim 1, wherein the promoter capable of expressing the protein under sugar-free conditions or in response to the depletion of sugar is a rice α-amylase RAmy3D promoter.

11. The method according to claim 1, wherein the target protein is hCTLA4Ig.

12. The method according to claim 1, wherein the plant cells are rice cells.

13. The method according to claim 12, wherein the rice cells are a cell line selected from the group consisting of Accession Numbers KCTC 10618BP, KCTC 10767BP and KCTC 10768BP.

* * * * *